(12) United States Patent
Hallett et al.

(10) Patent No.: US 11,725,066 B2
(45) Date of Patent: *Aug. 15, 2023

(54) PROCESS FOR THE EXTRACTION OF METAL POLLUTANTS FROM TREATED CELLULOSIC BIOMASS

(71) Applicant: IP2IPO Innovations Limited, London (GB)

(72) Inventors: Jason Hallett, London (GB); Paul Fennell, London (GB); Florence Gschwend, London (GB); Agnieszka Brandt-Talbot, London (GB); Geoffrey Kelsall, London (GB)

(73) Assignee: IP2IPO INNOVATIONS LIMITED, London (GB)

( * ) Notice: Subject to any disclaimer, the term of this patent is extended or adjusted under 35 U.S.C. 154(b) by 84 days.

This patent is subject to a terminal disclaimer.

(21) Appl. No.: 17/220,961

(22) Filed: Apr. 2, 2021

(65) Prior Publication Data

US 2021/0324112 A1    Oct. 21, 2021

Related U.S. Application Data

(63) Continuation of application No. 15/777,360, filed as application No. PCT/GB2016/053616 on Nov. 21, 2016, now Pat. No. 10,982,010.

(30) Foreign Application Priority Data

Nov. 20, 2015 (GB) .................................. 1520453

(51) Int. Cl.
| | |
|---|---|
| *C08B 1/00* | (2006.01) |
| *C08H 8/00* | (2010.01) |
| *B01D 11/02* | (2006.01) |
| *C07G 1/00* | (2011.01) |
| *C07H 3/02* | (2006.01) |
| *C12P 19/02* | (2006.01) |
| *C13K 1/02* | (2006.01) |

(52) U.S. Cl.
CPC .......... *C08B 1/003* (2013.01); *B01D 11/0288* (2013.01); *C07G 1/00* (2013.01); *C07H 3/02* (2013.01); *C08H 8/00* (2013.01); *C12P 19/02* (2013.01); *C13K 1/02* (2013.01)

(58) Field of Classification Search
None
See application file for complete search history.

(56) References Cited

U.S. PATENT DOCUMENTS

| | | |
|---|---|---|
| 2,032,437 A | 3/1936 | Richter |
| 3,598,695 A | 8/1971 | Waterstradt |
| 4,462,865 A | 7/1984 | Walles |
| 9,394,375 B2 | 7/2016 | Daly et al. |
| 9,765,478 B2 | 9/2017 | Brandt |
| 2007/0215300 A1 | 9/2007 | Upfal et al. |
| 2008/0164440 A1 | 7/2008 | Maase |
| 2008/0185112 A1 | 8/2008 | Argyropoulos |
| 2008/0190013 A1 | 8/2008 | Argyropoulos |
| 2008/0190321 A1 | 8/2008 | Maase et al. |
| 2008/0295980 A1 | 12/2008 | Hallberg |
| 2009/0234146 A1 | 9/2009 | Cooney et al. |
| 2010/0006245 A1 | 1/2010 | Myllymaki et al. |
| 2010/0081798 A1 | 4/2010 | Balensiefer et al. |
| 2010/0159521 A1 | 6/2010 | Cirakovic et al. |
| 2010/0279372 A1 | 11/2010 | Cho |
| 2011/0073805 A1 | 3/2011 | Dibble et al. |
| 2011/0124056 A1 | 5/2011 | Levie et al. |
| 2012/0010334 A1 | 1/2012 | D'Andola et al. |
| 2012/0245336 A1 | 9/2012 | Daly et al. |
| 2012/0325421 A1 | 12/2012 | Li et al. |
| 2013/0302854 A1 | 11/2013 | Tabata |
| 2014/0005451 A1 | 1/2014 | Mezza et al. |
| 2014/0073016 A1 | 3/2014 | Brandt et al. |
| 2015/0361616 A1* | 12/2015 | Essaddam ................ D21C 9/02 162/73 |
| 2016/0040354 A1 | 2/2016 | Hallett et al. |
| 2019/0241679 A1 | 8/2019 | Hallet et al. |

FOREIGN PATENT DOCUMENTS

| | | |
|---|---|---|
| CN | 101298620 A | 11/2008 |
| CN | 101333777 A | 12/2008 |
| CN | 101787381 A | 7/2010 |
| CN | 103556904 | 2/2014 |
| EP | 2669382 | 4/2013 |
| GB | 892744 | 3/1962 |
| IN | 2017/MUM/2008 | 2/2009 |
| WO | 9011401 A1 | 10/1990 |
| WO | 9849390 A1 | 11/1998 |
| WO | 2005017001 A1 | 2/2005 |
| WO | 2005017252 A1 | 2/2005 |
| WO | 2006108861 A1 | 10/2006 |
| WO | 2008073186 A2 | 6/2008 |
| WO | 2008090155 A1 | 7/2008 |
| WO | 2008090156 A1 | 7/2008 |
| WO | 2008112291 A2 | 9/2008 |
| WO | 2009105236 | 8/2009 |
| WO | 2010056790 A1 | 5/2010 |
| WO | 2012080702 A2 | 6/2012 |
| WO | 2012174459 | 12/2012 |
| WO | 20140113884 | 7/2014 |
| WO | WO-2014140643 A1 * | 9/2014 ............... C07G 1/00 |

OTHER PUBLICATIONS

A. Brandt et al., "Ionic liquid pretreatment of lignocellulosic biomass with ionic liquid-water mixtures," Green Chem., 13, 2589-2499 (2011).

Isikgor, F. and Becer, C., "Lignocellulosic biomass: a sustainable platform for the production of bio-based chemicals and polymers," Polymer Chemistry, 6(25), 4497-4559 (2015).

(Continued)

*Primary Examiner* — Dale R Miller
(74) *Attorney, Agent, or Firm* — McDonnell Boehnen Hulbert & Berghoff LLP

(57) ABSTRACT

The present invention relates to a process for extracting oxidised metal pollutants from treated cellulosic or lignocellulosic biomass to recover the metal. The treatment also generates a cellulosic or lignocellulosic biomass which can to be used as a feedstock for biofuel, for making cellulose containing materials, and provides a source of other renewable chemicals.

25 Claims, 3 Drawing Sheets

(56) References Cited

OTHER PUBLICATIONS

A. Brandt et al., "Deconstruction of lignocellulosic biomass with ionic liquids," Green Chem., 15, 550-83 (2013).
S.H. Lee et al., "Ionic Liquid-Mediated Selective Extraction of Lignin From Wood Leading to Enhanced Enzymatic Cellulose Hydrolysis," Biotechnology & Bioengineering, 102(5), 1368-76 (2009).
International Search Report issued in co-pending International Application No. PCT/GB2014/050824, European Patent Office, dated Jun. 3, 2014, 5 pages.
Written Opinion issued in co-pending International Application No. PCT/GB2014/050824, European Patent Office, dated Jun. 3, 2014, 6 pages.
"Determination of Structural Carbohydrates and Lignin in Biomass," NREL/TB-510-042618, National Renewable Energy Laboratory, Technical Report revised Aug. 2012, 18 pages.
"Preparation of Samples for Compositional Analysis," NREL/TP-510-42620, National Renewable Energy Laboratory, Technical Report dated Aug. 6, 2008, 12 pages.
"Determination of Total Solids in Biomass and Total Dissolved Solids in Liquid Process Samples," NREL/TP-510-42621, National Renewable Energy Laboratory, Technical Report issued Mar. 31, 2008, 9 pages.
"Enzymatic Saccharification of Lignocellulosic Biomass," NREL/TP-510-42619, National Renewable Energy Laboratory, Technical Report issued Mar. 21, 2008, 8 pages.
"Determination of Extractives in Biomass," NREL/TP-510-42619, National Renewable Energy Laboratory, Technical Report issued Jul. 17, 2005, 12 pages.
Brandt et al., "The effect of the ionic liquid anion in the pretreatment of pine wood chips," Green Chemistry, 2010, vol. 12, 672-679.
Fu et al., "Lignin Extraction from Straw by Ionic Liquids and Enzymatic Hydrolysis of the Cellulosic Residues," J. Agric. Food Chem., 2010, 58, 2915-292.
Lei et al., "Electrocoagulation Treatment of Chemithermomechanical Pulp (CTMP) Chemical Pretreatment Effluent," Bioinformatics and Biomedical Engineering (ICBBE), 2010 4th International Conference On, IEEE, Piscataway, NJ, USA Jun. 18, 2010, pp. 1-4.
Hulsbosch et al., "Biobased Inion Liquids: Solvents for a Green Processing Industry?," ACS Sustainable Chemistry & Engineering, vol. 4, No. 6, May 3, 2016, pp. 2917-2931.
International Search Report and Written Opinion dated Feb. 20, 2017 for International Application No. PCT/GB2016/053616, 13 pages.
Combined Search and Examination Report dated May 23, 2016 for Great Britain Application No. GB15209453.0, 7 pages.

\* cited by examiner

PROCESS FOR THE EXTRACTION OF METAL POLLUTANTS FROM TREATED CELLULOSIC BIOMASS

This application is a continuation of U.S. patent application Ser. No. 15/777,360, filed May 18, 2018, which is a U.S. National Stage entry of International Patent Application no. PCT/GB2016/053616, filed Nov. 21, 2016, which claims the benefit of priority of United Kingdom Patent Application no. 1520453.0, filed Nov. 20, 2015, each of which is hereby incorporated herein by reference in its entirety.

The present invention relates to a process for extracting oxidised metal pollutants from treated cellulosic or lignocellulosic biomass to recover the metal. The treatment also generates a cellulosic or lignocellulosic biomass which can to be used as a feedstock for biofuel, for making cellulose containing materials, and provides a source of other renewable chemicals.

A significant portion of wood used in the construction industry is treated with metal based preservatives. This is done to protect the wood from attack by microbes and insects during service. The preservatives contain copper (II) and sometimes also chromium (VI) (as chromate) and arsenic (V) (as arsenic pentoxide). Other metal pollutants are also found in wood such as zinc (II), iron (II/III) and lead (II). The main applications for preservative treated wood are decks, fences, landscape architecture, playground equipment, docks, marinas, utility poles, bridges, highway sound barriers, roller coasters, wood foundations and mine shafts. These preservative formulations are toxic: copper (II) is toxic to aquatic life and arsenic (V) and chromium (VI) are known to be very toxic to any multicellular life including humans. Leaching from in-service-material is limited, although public health concerns have been raised. Apart from this, the non-degradability of the wood and toxicity of the preservatives pose a definitive problem when the wood is taken out of service.

Common preservative formulations used are alkaline copper quaternary (ACQ), copper azole (CA, Tanalith E) and micronized copper quaternary (MCQ), which all contain substantial amounts of copper (up to 3700 ppm). Chromated copper arsenate (CCA, Tanalith C), a mixture of CuO, $CrO_3$ and $As_2O_5$ has been used extensively between the 1930s until the early 2000s. Timber treated with CCA can contain over 5000 mg $kg^4$ of arsenic (V) and chromium (VI). This is the most hazardous wood treatment, hence CCA use was heavily curtailed in Europe and the US in 2003-2004. However, CCA treated timber still in service will pose a substantial problem for the next 20-40 years. Reportedly, up to $2.5 \times 10^6$ $m^3$ $a^{-1}$ of spent CCA-treated wood will be removed from service in the next 20 years in Canada. It has been estimated that $6-10 \times 10^6$ $m^3$ $a^{-1}$ of CCA-treated wood waste will be produced in the USA by 2030.

The treated timber is classified as hazardous waste and cannot be directly used in biomass-to-heat conversion or recycled into panel boards or similar, thus incurring high costs for specialist disposal, such as landfilling. Copper (II) only treated timber may be incinerated in monitored specialist boilers and the waste reduced to metal containing ash. In contrast, incineration of arsenic (V) containing wood is problematic, as the arsenic (V) compounds generated during thermal treatment are volatile and at least partially emitted into the atmosphere.

The following recovery methods of the metal additives from the treated wood are in being used or currently explored:

(1) Controlled landfill
   Landfills that are not in contact with the ground water table are deemed suitable for disposal of treated wood waste. However, landfill sites are becoming scarcer and landfilling is becoming expensive.

(2) Thermal treatment and disposal of metal enriched ash
   Boilers for thermal treatment of hazardous timber are not operated in the UK due to high demand on furnace specifications and monitoring (Regional Market Assessment for Wood Waste for North East England, 2007). However, thermal treatment may be feasible for wood treated with the newer, copper only, preservatives. Copper compounds are non-volatile and thus only a small percentage escapes as fly ash into the atmosphere upon combustion of the contaminated biomass (less than 7%). Processes deriving value from combustion, gasification or pyrolysis do not currently exist.

(3) Leaching and disposal of chemically precipitated metal ions
   Leaching of the oxidised metals from the wood has been proposed. Options discussed in the literature are
      a. Leaching with dilute acid solution or aqueous solutions containing chelating agents
      b. Complete dissolution of waste wood in concentrated sulfuric acid
   The metal-containing effluents are treated as heavy metal contaminated waste water (metal ions removed e.g. by flocculation and precipitation). Recovered wood can be incinerated as normal waste wood if the metal content is sufficiently low. The recovered wood cannot be used as a source of biofuel as the wood is decomposed during the process and not suitable for subsequent use in the saccharification process. Electrodeposition of $Cu^{II}$ from aqueous solution has been demonstrated recently. A recent study presented insights obtained from operating a pilot plant and the associated techno-economic model for dilute acid-leaching. It was estimated that the operating cost would be $250-289 $t^{-1}$ of treated wood. This shows that metal extraction should be integrated with a value-adding application.

The mentioned decontamination methods for metal containing timber are costly, in the area of $180 $t^{-1}$ waste timber. On the other hand, cost of virgin wood feedstock for biofuel production is estimated to be $80 $t^{-1}$. Currently, there are a handful of commercial-scale cellulosic biofuel plants in operation, all using virgin biomass (mostly agricultural residues and energy grasses) and steam based pretreatment technologies.

The use of contaminated waste wood as feedstock for a biorefinery would hence eliminate a waste management problem and increase the economic viability of lignocellulosic biomass for biofuel and biochemical production. Electrochemical recovery of the metals in a useful elemental form would further add value.

Lignocellulosic biomass, such as wood, consists of 3 major components arranged in an intricate, yet physically and chemically stable material. Approximately 40% of wood is cellulose. Cellulose is long chains of glucose arranged infibrils. They give wood its high strength and stiffness. Hemicellulose, 25 weight % of the material, acts as a filler matrix that binds the cellulose fibrils together. Lignin, also approximately 25% of the material, is a glue infused into the cellulose hemicellulose matrix, conferring elasticity and water-proofness. Cellulose and hemicellulose are long chains composed of sugars, while lignin's repeat units contain aromatic rings. For cellulosic biofuel production, the lignocellulosic matrix is opened up during pre-treatment/ fractionation (at elevated temperature). A separate fraction of cellulose is obtained. The sugar molecules can be released from washed cellulose using an enzymatic hydrolysis step. The resulting sugar solution can be converted to biofuels or other biochemicals by fermentation. If a preservative treated lignocellulosic biomass source was used, the presence of the metals e.g. copper from the preservatives would kill the microbes used in the fermentation step. Therefore, only virgin (untreated) biomass sources have been used to date. The lignin present in the lignocellulosic biomass can be used for energy recovery and production of renewable materials such as resins, polyols, carbon fibres and chemicals, depending on the extraction conditions and purity.

The fractionation of cellulose and lignin from lignocellulosic biomass using ionic liquids has been previously described in WO 2012/080702 and WO2014/140643.

The present invention describes a process of extracting metals from treated cellulosic or lignocellulosic biomass, such as wood, using an ionic liquid (IL). The ionic liquids fractionate metal containing cellulosic or lignocellulosic biomass waste into a cellulose rich solid material, and a liquid phase. The liquid phase comprises a hemicellulose fraction and a lignin fraction, and retains the metals in the IL solution. The cellulose rich material can be used to produce biofuels and plant derived chemicals. The metal, and optionally the lignin, can also be recovered from the IL, and the IL can be recycled.

Thus in the first aspect the invention provides a process for the extraction of metal pollutants from treated cellulosic biomass comprising contacting the treated cellulosic biomass with an ionic liquid, said ionic liquid comprising an anion and an organic cation. As used herein an "organic" cation refers to a cation containing carbon and hydrogen and optionally one or more heteroatoms such as oxygen, nitrogen, phosphorous and sulfur.

"Extraction" as used herein refers to the removal of metal ions from the treated cellulosic or lignocellulosic biomass. The metal ions dissolve in the ionic liquid. The extraction process removes sufficient metal so that fermentation of the cellulose rich material produced is not inhibited by the presence of the metal pollutants. At least 50% of the metal present in the treated cellulosic or lignocellulosic biomass is removed, more preferably at least 60%, 70%, 75%, 80%, 85%, 90%, 95% or 99% of the metal present. Most preferably the process removes at least 85% of the metal present.

As used herein the term "cellulosic" or "lignocellulosic biomass" refers to living or dead biological material that can be used in one or more of the disclosed processes. It can comprise any cellulosic or lignocellulosic material and includes materials comprising cellulose, and optionally further comprising hemicellulose, lignin, starch, oligosaccharides and/or monosaccharides, biopolymers, natural derivatives of biopolymers, their mixtures, and breakdown products. It can also comprise additional components, such as protein and/or lipid. The biomass can be derived from a single source, or it can comprise a mixture derived from more than one source. Some specific examples of biomass include, but are not limited to, bioenergy crops, agricultural residues, municipal solid waste, industrial solid waste, sludge from paper manufacture, sewage sludge, residue from composting, food waste, spent distilling grain, spent Brewer's yeast, anaerobic digestive, yard waste, wood and forestry waste. Additional examples of biomass include, but are not limited to, corn grain, corn cobs, crop residues such as corn husks, corn stover, grasses including *Miscanthus X giganteus, Miscanthus sinensis* and *Miscanthus sacchariflorus*, wheat, wheat straw, hay, rice straw, switchgrass, waste paper, sugar cane bagasse, sorghum, soy, components obtained from milling of grains, trees (e.g. pine), branches, roots, leaves, wood chips, wood pulp, sawdust, shrubs and bushes, vegetables, fruits, flowers, animal manure, multi-component feed, and crustacean biomass (i.e., chitinous biomass). It may be preferable to treat the biomass before use in the method of the invention. For example the biomass could be mechanically treated e.g. by milling or shredding.

Preferably, the treated cellulosic biomass is a treated lignocellulosic biomass. "Treated cellulosic" or "treated lignocellulosic biomass" as used herein refers to wood or other cellulose or lignocellulose containing biomass which has been processed so that it contains metal or metal ions (metal pollutants). For example it has been treated with a preservative or other metal-based formulation e.g. copper-based fungicide. The preservative is preferably a metal based preservative such as one containing an alkaline copper quaternary (ACQ), copper azole (CA, Tanalith E), micronized copper quaternary (MCQ), or Chromated copper arsenate (CCA, Tanalith C). It also includes wood or other cellulosic or lignocellulosic biomass which has been painted for example with a lead-based paint, or paint containing titanium dioxide. Other forms of treated cellulosic or lignocellulosic biomass include sewage sludge, which may contain cadmium (II) and/or mercury (I/11), waste paper and municipal solid waste which may contain titanium as titanium dioxide. Preferably the treated cellulosic biomass is a lignocellulosic biomass, such as wood treated with a preservative.

A "metal pollutant" as used herein is a metal present within the cellulosic or lignocellulosic biomass which is not present in the cellulosic or lignocellulosic biomass in its natural state. The metal pollutant is preferably present as an oxidised metal compound or metal ions. In particular it refers to a metal which inhibits the downstream hydrolysis and/or fermentation of the cellulose rich material derived from the cellulosic or lignocellulosic biomass. The metal is preferably selected from zinc (II), lead (II), copper (II), arsenic (V), iron (II/III), titanium and chromium (VI). Preferably the metal is selected from copper (II), arsenic (V) or chromium (VI), more preferably copper (II). The metal is preferably derived from a preservative.

The IL is preferably heated with the biomass at 100-180° C., preferably 120-170° C. The reaction is carried out for 5 min-22 hours, preferably 20 min-13 hours, more preferably 30 min-8 hours i.e. 10, 15, 20, 30, 45 min, 1 hr, 2 hr, 3 hr, 4 hr, 5 hr, 6 hr, 7 hr, 9 hr, 10 hr, 11 hr, 12 hr, 15 hr, 17 hrs, 20 hrs and ranges there between. Preferably the mixture is stirred, for example at 50-200 rpm.

As used herein "ionic liquid" refers to an ionized species (i.e. cations and anions). Typically they have a melting point below about 100° C. It is important to choose an ionic liquid which is both thermally and chemically stable, so that is does not decompose during the treatment process or electrodeposition. The ionic liquid comprises one or more anion with one or more cation.

The anion is preferably selected from $C_{1-20}$alkyl sulfate [Alkyl $SO_4$]$^-$, chloride [Cl]$^-$, bromide [Br]$^-$, hydrogen sulfate [$HSO_4$]$^-$, hydrogen sulfite [$HSO_3$]$^-$, Trifluoromethanesulfonate [OTf]$^-$ and acetate [OAc]$^-$ or mixtures thereof. More preferably the anion is chloride [Cl]$^-$, or hydrogen sulfate [$HSO_4$]$^-$.

Preferably but not essentially, the lignin in the wood or lignocellulosic biomass is soluble in the ionic liquid at the treatment temperature, but the cellulose is not, so that a solid residue or pulp comprising the cellulose is produced. Other components such as hemicellulose may preferably also dissolve in the ionic liquid. The metal pollutants are retained in the ionic liquid.

The cation is preferably a protic cation ion, i.e. they are capable of donating a $H^+$ (proton).

The cation ion can be an ammonium derivative. These cations have the general formula

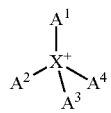

wherein

X is N; and $A^1$ to $A^4$ are each independently selected from H, an aliphatic, $C_{3-6}$ carbocycle, $C_{6-10}$ aryl, alkylaryl, and heteroaryl.

Preferably at least one of $A^1$ to $A^4$ is H. Preferably $A^1$ to $A^4$ are each independently selected from H, and an aliphatic. In one embodiment one of $A^1$ to $A^4$ is H, and the remaining three are each independently an aliphatic. Alternatively two of $A^1$ to $A^4$ are each H and the remaining two are each independently an aliphatic. Alternatively one of $A^1$ to $A^4$ is an aliphatic, and the remaining three are all H. Preferably the cation is not ammonium ($NH_4^+$.) i.e. at least one of $A^1$ to $A^4$ is not H.

The term "aliphatic" as used herein refers to a straight or branched chain hydrocarbon which is completely saturated or contains one or more units of unsaturation. Thus, aliphatic may be alkyl, alkenyl or alkynyl, preferably having 1 to 12 carbon atoms, preferably up to 6 carbon atoms or more preferably up to 4 carbon atoms. The aliphatic can have 1, 2, 3, 4, 5, 6, 7, 8, 9, 10, 11, or 12 carbon atoms.

The term "alkyl" as used herein, is typically a linear or branched alkyl group or moiety containing from 1 to 20 carbon atoms, such as 11, 12, 13, 14, 15, 16, 17, 18, or 19 carbon atoms. Preferably the alkyl group or moiety contains 1-10 carbon atoms i.e. 2, 3, 4, 5, 6, 7, 8, 9, or 10 carbon atoms such as a $C_{1-4}$ alkyl or a $C_{1-6}$ alkyl group or moiety, for example methyl, ethyl, n-propyl, i-propyl, n-butyl, i-butyl and t-butyl, n-pentyl, methylbutyl, dimethylpropyl, n-hexyl, 2-methylpentyl, 3-methylpentyl, 2,3-dimethylbutyl, and 2,2-dimethylbutyl.

As used here in the term "alkenyl" refers to a linear or branched alkenyl group or moiety containing from 2 to 20 carbon atoms, such as 11, 12, 13, 14, 15, 16, 17, 18, or 19 carbon atoms. Preferably the alkyl group or moiety contains 2-10 carbon atoms i.e. 3, 4, 5, 6, 7, 8, 9, or 10 carbon atoms such as a $C_{2-4}$ alkenyl or a $C_{2-6}$ alkenyl group or moiety, for example ethenyl, 2-propenyl, 1-propenyl.

The term "carbocycle" as used herein refers to a saturated or partially unsaturated cyclic group having 3 to 6 ring carbon atoms, i.e. 3, 4, 5, or 6 carbon atoms. A carbocycle is preferably a "cycloalkyl", which as used herein refers to a fully saturated hydrocarbon cyclic group. Preferably, a cycloalkyl group is a $C_3$-$C_6$ cycloalkyl group.

The term "$C_{6-10}$ aryl group" used herein means an aryl group constituted by 6, 7, 8, 9 or 10 carbon atoms and includes condensed ring groups such as monocyclic ring group, or bicyclic ring group and the like. Specifically, examples of "$C_{6-10}$ aryl group" include phenyl group, indenyl group, naphthyl group or azulenyl group and the like. It should be noted that condensed rings such as indan and tetrahydro naphthalene are also included in the aryl group.

The terms "alkylaryl" as used herein refers to an alkyl group as defined herein substituted with an aryl as defined above. The alkyl component of an "alkylaryl" group may be substituted with any one or more of the substituents listed above for an aliphatic group and the aryl or heteroaryl component of an "alkylaryl" or "alkylheteroaryl" group may be substituted with any one or more of the substituents listed above for aryl, and carbocycle groups. Preferably, alkylaryl is benzyl.

The term "heteroaryl" as used herein refers to a monocyclic or bicyclic aromatic ring system having from 5 to 10 ring atoms, i.e. 5, 6, 7, 8, 9, or 10 ring atoms, at least one ring atom being a heteroatom selected from O, N or S.

An aryl, heteroaryl, or carbocycle group as referred to herein may be unsubstituted or may be substituted by one or more substituents independently selected from the group consisting of halo, lower alkyl, —$NH_2$, —$NO_2$, —OH —COOH, or —CN.

The term "halogen atom" or "halo" used herein means a fluorine atom, a chlorine atom, a bromine atom, an iodine atom and the like, preferably a fluorine atom or a chlorine atom, and more preferably a fluorine atom.

Preferably the cation is an alkylammonium or a mixture thereof, preferably protic alkylammoniums, although aprotic alkylammoniums may also be used. Optionally one or more of the alkyl groups may be substituted with —OH to form an alkanolammonium, which can also be referred to as an alcoholammonium. As used herein an "alkylammonium" includes tetraalkylammoniums, trialkylammoniums, dialkylammoniums, monoalkylammoniums, and alcoholammoniums including trialcoholammoniums, dialcoholammoniums and monoalcoholammonium. Trialkylammoniums include trimethylammonium, triethylammonium, and triethanolammonium. Examples of dialkylammoniums include diethylammonium, diisopropylammonium, and diethanolammonium. Monoalkylammoniums include methylammonium, ethylammonium, and monoethanolammonium.

Preferably the tetraalkylammonium is aprotic, i.e. not capable of acting as a proton donor.

Preferred alkylammonium cations are triethylammonium, diethylammonium dimethylethylammonium, diethylmethylammonium, dimethylbutylammonium and diethanolammonium.

The ionic liquid may contain one of the listed ammonium cations, or a mixture thereof.

The cation can also contain a nitrogen-containing heterocyclic moiety which, as used herein, refers to mono- or bicyclic ring systems which include one nitrogen atom and optionally one or more further heteroatoms selected from N, S and O. The ring systems contain 5-9 members, preferably 5 or 6 members for monocyclic groups, and 9 or 10 members for bicyclic groups. The rings can be aromatic, partially saturated or saturated and thus, includes both a "heteroalicyclic" group, which means a non-aromatic heterocycle and a "heteroaryl" group, which means an aromatic heterocycle. The cation is preferably selected from

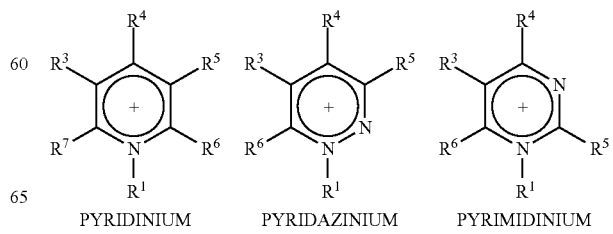

PYRIDINIUM    PYRIDAZINIUM    PYRIMIDINIUM

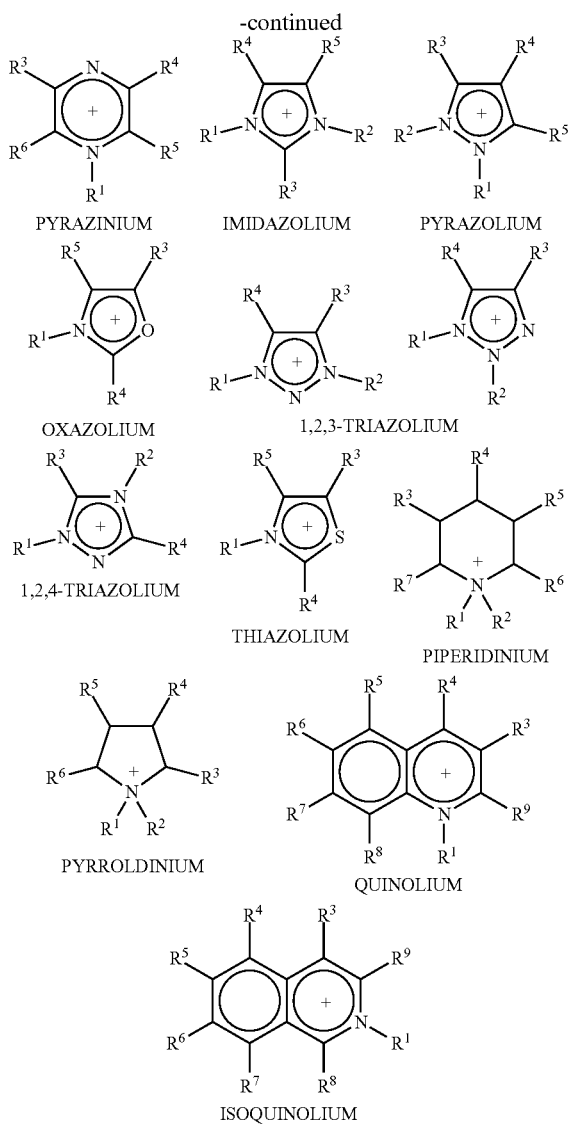

wherein $R^1$ and $R^2$ are independently selected from H, a $C_{1-6}$ alkyl or a $C_{1-6}$ alkoxyalkyl group, and $R^3$, $R^4$, $R^5$, $R^6$, $R^2$, $R^8$ and $R^9$, when present are independently H, a $C_{1-6}$ alkyl, $C_{1-6}$ alkoxyalkyl group, or $C_{2-6}$ alkyoxy group. Preferably $R^1$ and $R^2$ are $C_{1-4}$ alkyl, with one being methyl and $R^3$—$R^9$, ($R^3$, $R^4$, $R^5$, $R^6$, $R^2$, $R^8$ and $R^9$), when present, are H. Preferably the cation ring is imidazolium or pyridinium.

"$C_{2-6}$ Alkoxy" refers to the above $C_{1-6}$ alkyl group bonded to an oxygen that is also bonded to the cation ring. A "$C_{2-6}$ alkoxyalkyl group" refers to an alkyl containing an ether group, with the general formula X—O—Y wherein X and Y are each independently a $C_{1-5}$ alkyl and the total number of carbon atoms is between 2 and 6 e.g. 2, 3, 4, 5, or 6.

Preferred cations are imidazolium based cations or a mixture thereof in particular protic imidazolium based cations. Preferably the imidazolium based cations is selected from 1-ethyl-3-methylimidazolium ([EMIM]+), 1-butylimidazolium ([HBIM] 1 and 1-methylimidazolium ([HMIM]+, also referred to as [HC₁im]+ herein) or a mixture thereof.

Preferred cations include protic alkylammonium, protic methylimidazolium, protic pyridinium, aprotic tetraalkylammonium and aprotic dialkylimidazolium ions.

The ionic liquid may contain one of the listed cations, or a mixture thereof.

Preferred ionic liquids for use in the invention are triethylammonium hydrogen sulfate [TEA][HSO₄], N,N-dimethyl-N-butylammonium hydrogen sulfate [DMBA][HSO₄], 1-methylimidazolium hydrogen sulfate [HMIM][HSO₄], I butylimidazolium hydrogen sulfate [HBIM][HSO₄], diethylammonium hydrogen sulfate [DEA][HSO₄], diethanolammonium Chloride [DEtOHA][Cl], 1-methylimidazolium hydrogen chloride [HMIM][Cl], 1-ethyl-3-methylimidazolium chloride [EMIM][Cl], 1-ethyl-3-methylimidazolium acetate [EMIM][OAc], 1-ethyl-3-methylimidazolium trifluoromethanesulfonate [EMIM][OTf]. Particularly preferred ionic liquids are 1-methylimidazolium hydrogen sulfate [HMIM][HSO₄] and 1-methylimidazolium chloride [HMIM][Cl].

Ionic liquids can be prepared by methods known to the person skilled in the art or obtained commercially. For example, the ILs can be made from a simple alkylamine, such as triethylamine, and sulfuric acid in a one-step synthesis, for example as described in George et al., (2015) "Design of low-cost ionic liquids for lignocellulosic biomass treatment" Green Chemistry 17:1728-173.

Usually in an ionic liquid the cation and anion are present in equimolar amounts. However, the ionic liquid may preferably comprise excess base, preferably protonated base. 'Base' as used herein refers to the base from which the cation is derived e.g. amine/imidazole. Preferably the ionic liquid comprises 10% molar excess base, preferably 4-8%, 5-7.5% excess base. The ionic liquid may comprise 2%, 3%, 4%, 5%, 6%, 7%, 8% 9% or 10% molar excess base.

It has been surprisingly found that the yield in the saccharification step can be improved if the ionic liquid composition comprises water. Therefore in one preferred embodiment the composition comprises the IL and 10-40% v/v water. Preferably the composition comprises 20-30% v/v water. Water is added at around 20% to prevent reactions between IL and treated cellulosic or lignocellulosic biomass, reduce viscosity and promote depolymerisation of lignin.

It has also been discovered that the presence of an excess of acid accelerates the pre-treatment resulting in improved lignin removal and thus enhanced saccharification yields, as lignin interferes with the enzyme binding. Thus, the glucose yield is improved. Therefore in one preferred embodiment the composition further comprises 0.01-20% molar excess acid, preferably 1-5% molar excess acid, as a percentage of the IL. The addition of a small amount of acid significantly accelerates the pre-treatment process, when other variables such as water content and temperature are kept constant. The acid can be selected from any known strong acid such as hydrochloric acid, sulfuric acid, nitric acid, phosphoric acid hydroiodic acid, perchloric acid and hydrobromic acid. Preferably the acid is sulfuric or, hydrochloric or phosphoric acid.

In a preferred embodiment the treated cellulosic or lignocellulosic biomass is contacted with the ionic liquid composition prior to mechanical treatment. It has been found that contacting the treated cellulosic or lignocellulosic biomass with the ionic liquid can reduce the energy required to grind the treated cellulosic or lignocellulosic biomass. The IL composition appears to work as a lubricant during the grinding phase. The treated cellulosic or lignocellulosic biomass can be impregnated briefly with an IL composition at slightly elevated temperature (70-100° C., preferably 90° C.) to harness their lubrication properties before a mechanical size reduction step is applied. The IL composition can be contacted with the treated cellulosic or lignocellulosic biomass for any length of time from several minutes to 18 hours or longer, preferably 5 minutes to 1 hour. This can be followed by further treatment with an ionic liquid composition as described herein to extract the metal pollutants and also solubilise the lignin content of the treated lignocellulosic biomass.

This invention adds a novel aspect to the fractionation of cellulosic or lignocellulosic biomass with ionic liquids by integrating the cellulose or lignocellulose fractionation with pollutant metal extraction. As described in the examples, pre-treatments with an ionic liquid of softwood impregnated with a copper-based preservative achieved up to 98% removal of the $Cu^{II}$ in a single pass.

The metal can be recovered from the IL, thereby providing an additional income stream, and by removing the metal pollutant increases the value of biomass utilised, as the cellulosic or lignocellulosic biomass will be converted from a negative-value waste into a positive-value fuel resource (FIG. 1). Cellulosic biofuel production and hazardous waste wood processing in one step has not been described previously.

Ionic liquids are highly conductive solvents due to their ionic nature and regarded as superior media for the electrodeposition of metals and semiconductors. Key advantages that enable the ILs to overcome the limits imposed by common aqueous or organic media are their wide electrochemical windows, spanning up to 6 V in some cases; low vapour pressures, which allow electrodeposition at temperatures well above 100° C., and numerous, only partly understood, cation/anion effects that make it possible to influence the morphology and crystal size of deposits. Electrodeposition is currently not practised for the recovery of metals from dilute heavy metal-containing IL waste streams.

The process may preferably further comprise electrodeposition of the metal pollutant from the ionic liquid. The electrodeposition can be carried out by applying an appropriate current per unit electrode area from a transformer-rectifier, as used industrially for recovery of many metals from aqueous electrolyte solutions. Other suitable methods include chronoamperometry and chronopotentiometry. Electrodeposition allows the metal pollutant to be recovered as a solid metal or alloy. Recovery of metals by electrodeposition provides an added revenue stream which could provide $10 worth (assuming a price of $5,000 (tonne $Cu)^{-1}$) of $Cu^0$ per tonne of treated wood (containing 2000 ppm of $Cu^{II}$). The electrical energy costs required for the process are estimated as an order of magnitude lower than the value of the recovered copper. The process also eliminates the need to landfill metal containing ashes. In addition recycling of metals may contribute to a reduced reliance on foreign imports of metals (strengthen local resource resilience) and also reduce the environmental impact of mining.

After the electrodeposition process, the ionic liquid can be recycled or re-used to process further treated cellulosic or lignocellulosic biomass in step (a) and/or step (ci).

The ionic liquids of the present invention dissolve the lignin within the biomass but do not dissolve the cellulose. The majority of cellulose remains solid, preferably at least 90%, more preferably 95%. It can be easily removed from the liquid phase mechanically, for example by filtration. The separated solid residue or pulp can then be washed and used in the saccharification process. This removes the need for a separate precipitation step to obtain the cellulose once the biomass has been treated. Thus the method of the invention may preferably further comprise the step of separating the ionic liquid from the cellulose containing solid residue produced in step (a) from the ionic liquid.

The cellulose containing solid residue may be washed with ionic liquid or an organic solvent miscible with the ionic liquid. The separation efficiency and the ionic liquid recovery can be enhanced by washing the cellulose containing solid residue with ionic liquid or an organic solvent that is miscible with the ionic liquid. Examples of suitable organic solvents include aliphatic alcohols such as methanol and ethanol. After washing, the organic solvent can be separated from the cellulose containing solid residue, and added to the ionic liquid from step (a). The organic solvent is removed before or potentially after the lignin is precipitated. The organic solvent can be removed from the ionic liquid using conventional methods known to the skilled person. For example the volatile organic solvents can be removed by distillation.

It is possible to precipitate the lignin dissolved in the IL compositions. Therefore the method may further comprise
   (d) adding an anti-solvent to the ionic liquid which has been separated from the cellulose containing solid residue produced in step (a), to precipitate out the dissolved lignin and optionally separating the precipitated solid from the anti-solvent/ionic liquid.

As used herein an "anti-solvent" or precipitate is a liquid which causes the lignin to precipitate out from the ionic liquid containing the solubilised lignin produced in step (a). The anti-solvent is preferably water or ethanol. The ionic liquid can be recovered by removing the anti-solvent, for example by evaporation. The resulting ionic liquid can then be recycled to be used again in the method. Thus the method may further comprise removing the anti-solvent from the ionic liquid obtained in (d).

The ionic liquid may need to be dried to remove excess water. The water may be removed by conventional methods such as evaporation. The water may be removed after step (a) and/or after the lignin has been precipitated. As the presence of some water improves the yield less energy is required to dry the IL.

The cellulose containing solid residue obtained from the method of the invention can undergo saccharification, for example by enzymatic hydrolysis, to obtain glucose. The glucose can then be used in a fermentation process to obtain biofuel. Therefore the process can further comprise saccharification of the cellulose containing solid residue to obtain glucose. The cellulose containing solid residue used in the saccharification step may be the cellulose containing solid residue obtained in the initial step, step (a), or the washed solid residue obtained in step (c). The invention also provides a cellulose containing solid residue obtained by a suitable method of the invention; for example as obtained by the process comprising any one or more of steps (a-c). In a further aspect the invention provides a process of preparing glucose from treated cellulosic or lignocellulosic biomass comprising subjecting a cellulose containing solid residue obtained by suitable methods of the invention to enzymatic hydrolysis. In a further aspect the invention provides glucose obtained by this hydrolysis.

Suitable enzymes for use in the process include commercially available preparations of cellulases such as *T. reseei* cellulase and Novozyme 188 cellobiase that also contains hemicellulolytic activity. Other useful enzymes include esterases, either acetyl esterases or feruloyl esterases, which cleave substituents that are esterified to hemicellulose. The process is preferably carried out in an aqueous medium at a suitable pH for the enzymes. The conditions can be optimised in relation to pH, temperature and the medium used depending on the enzyme mixture required. Such methods are well known to the skilled person. The process is preferably carried out in accordance with "Enzymatic saccharification of lignocellulosic biomass" (NREL/TP-510-42629), issue date Mar. 21, 2008.

In summary the process of the invention may comprise the following steps:
- (a) contacting the treated cellulosic or lignocellulosic biomass with an ionic liquid, said ionic liquid comprising an anion and a cation;
- (b) optionally separating the cellulose containing solid residue obtained in step (a) from the ionic liquid;
- (c) optionally washing the cellulose containing solid residue at least once with ionic liquid or an organic solvent miscible with the ionic liquid; and separating the cellulose containing solid residue from the ionic liquid or organic solvent and optionally adding the ionic liquid or organic solvent to the ionic liquid obtained in (b);
- (d) optionally adding an anti-solvent to the ionic liquid obtained in (b) to precipitate the lignin;
- (e) optionally removing water from the ionic liquid, after step (b) and/or after step (d);
- (f) electrodeposition of the metal pollutant from the ionic liquid obtained in steps (b), and/or (c) and/or (e);
- (g) optionally recycling the ionic liquid after step (f) to be used in step (a) and/or step (c); and
- (h) optionally saccharification of the cellulose containing solid residue obtained in any of steps (a), (b) and/or (c) to obtain glucose.

The invention further provides for the use of an ionic liquid as defined herein to extract metal from a treated cellulosic or lignocellulosic biomass source, preferably a wood source which has been treated with a preservative, in particular a metal based preservative. The invention further provides the use of an ionic liquid as defined herein, ins a method of extraction metal from a treated cellulosic or lignocellulosic biomass source as described herein.

The invention will now be described in the examples below which refer to the following figures:

FIG. 1 is a flow chart of the biomass pre-treatment and copper extraction process. CRM stands for Cellulose Rich Material.

FIG. 2 displays the composition of the copper (II) treated wood as analysed by compositional analysis.

The temperature and time period are not essential for the extraction of the copper (II), but they will have a major impact on the sugar yields achieved from enzymatic saccharification of the pulps.

EXAMPLE 1. DECONSTRUCTION OF BIOMASS AND EXTRACTION OF METALS IN VARIOUS IONIC LIQUIDS

Figure 1:
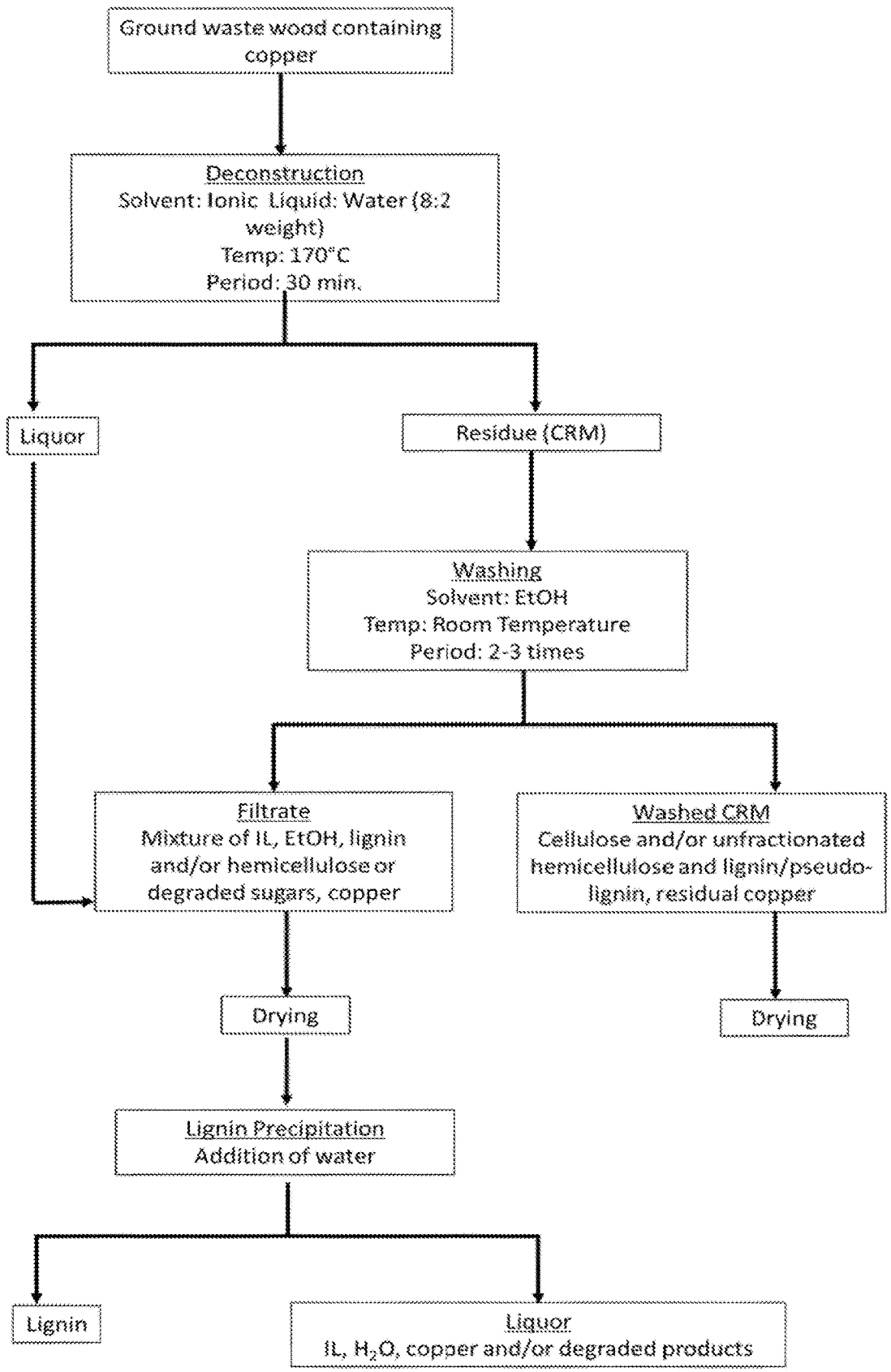

A flow chart of the deconstruction and extraction process is summarized in FIG. 1. An ionic liquid/water mixture was prepared by adding the required amount of water to the dried ionic liquid. The water content was confirmed by Karl-Fischer titration in triplicate. Pre-treatments were run in triplicate. 10±0.05 g of ionic liquid/water master-mix was weighed into a glass pressure tube and the exact weight recorded. Copper azole treated softwood (1.0 g oven-dried basis) with particle sizes of 180-850 μm was added and the tube tightly closed and the contents mixed with a Vortex shaker until all of the biomass had been in contact with the ionic liquid. The vial was placed in a preheated convection oven at 170° C. for 30 min. After the incubation, the mixture was transferred into a 50 mL centrifuge tube. This was facilitated by diluting with 40 mL of ethanol. The contents were mixed using a vortex shaker and left at room temperature for one hour. The tube was then centrifuged and the solids and liquids decanted carefully into a round bottom flask. The solid was further washed by repeating the washing step 2-3 more times. The remaining solid (pulp) was then transferred into a cellulose thimble and further washed by Soxhlet extraction with refluxing ethanol (150 mL) for 22 hours. The pulp was left to dry in the thimble on the bench overnight. The ethanol used for the Soxhlet extraction was combined with the previous washes and evaporated under reduced pressure at 40° C., leaving the dried ionic liquid/lignin mixture. To the dried ionic liquid/lignin mixture, 30 mL of water was added in order to precipitate the lignin. The suspension was transferred into a 50 mL falcon tube, shaken for one minute and then left at room temperature for at least 1 hour. The tube was centrifuged and the supernatant decanted and collected in a round bottom flask. This washing step was repeated three more times and the washings combined.

The air-dried pulp yield was determined by weighing the recovered biomass from the cellulose thimbles. The oven-dried yield was determined as described below. The lid of the centrifuge tube containing the lignin was pierced and the tube put into a vacuum oven overnight for drying the lignin at 40° C. under vacuum. The dried lignin was weighed the next day to determine the lignin yield.

Saccharification

Enzymatic saccharification was performed in triplicate according to LAP "Enzymatic saccharification of lignocellulosic biomass" (NREL/TP-510-42629), issue date Mar. 21, 2008. The enzymes were Novozymes experimental enzyme mixture NS-22201. Glucose yields were calculated based on the glucose content of the untreated biomass. 50 μL of enzyme solution was used per 100 mg of sample.

Compositional Analysis

The glucan, hemicellulose and lignin content of copper treated timber was determined following the LAP procedures "Preparation of samples for compositional analysis" (NREL/TP-510-42620), issue date Aug. 6, 2008 and Determination of Structural Carbohydrates and Lignin in Biomass" (NREL/TP-510-42618 version Aug. 3, 2012). The extractives in untreated copper treated timber were removed and quantified according to the LAP "Determination of extractives in biomass" (NREL/TP-510-42619), issued Jul. 17, 2005. The oven-dry weight (ODW) of lignocellulosic biomass was determined according to the procedure described in the LAP "Determination of Total Solids in Biomass and Total Dissolved Solids in Liquid Process Samples" (NREL/TP-510-42621) issued Mar. 31, 2008.

Metal Content

Inductively coupled plasma optical emission spectrophotometry (ICP-OES) was used to analyse the ionic liquid liquor on its metal content and run in triplicate on a Perkin Elmer Optima 2000 DB instrument. A mixed metal standard for ICP analysis was obtained from Sigma Aldrich (TraceCERT grade) and diluted to the required concentrations with 5% nitric acid.

The water content of the ionic liquid liquors was determined by Karl-Fischer titration. The liquors were diluted to below 10 ppm of copper and a maximum of 1 wt % ionic liquid concentration with 5% nitric acid and then analysed by ICP-OES.

Approximately 100 mg of ground wood samples were weighed out and the exact weight recorded (±0.1 mg, Mettler Toledo NewClassic MS). The samples were digested in 1 mL 69% nitric acid in a closed PTFE vessel (MARSXpress vessels and microwave with power/time control by CEM with the following sequence: 300 W at 83% power for 5 min, 600 W at 66% power for 5 min and 1200 W at 58% power for 6 min). The obtained solution was cooled in a freezer for an hour before diluting to 10 mL with 5% nitric acid and filtration through a 0.4 μm PTFE syringe filter.

The measured wood's copper content was used to calculate the percentage of copper extracted into the ionic liquid.

Results and Discussion

Figure 2:
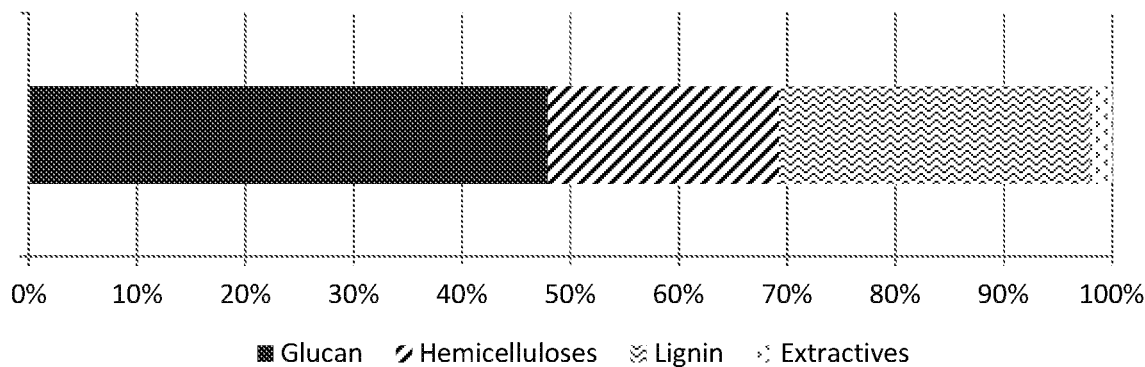

Ionic Liquid Screening Experiments for the Extraction of Copper(II) from CA Treated Softwood FIG. 2 displays the composition of the copper treated wood as analysed by compositional analysis.

TABLE 1

Composition of copper treated wood used in pre-treatments. Glu stands for glucan, Xyl for xylan, Gal for galactan, Ara for arabinan, Man for mannan, AIL for acid insoluble lignin, ASL for acid soluble lignin, Extr. for extractives.

| Glu | Xyl | Gal | Ara | Man | AIL | ASL | Ash | Extr. |
|---|---|---|---|---|---|---|---|---|
| 47.9 ± 0.8 | 6.5 ± 0.1 | 0.8 ± 0.0 | 0.4 ± 0.0 | 13.6 ± 0.3 | 25.4 ± 1.1 | 3.3 ± 0.1 | BDL | 2.1 ± 0.0 |

The following ionic liquids were screened for their suitability to fractionate/pre-treat biomass and to extract copper from the biomass, where [TEA] stands for triethylammonium, [DMBA] for N,N-dimethyl-N-butylammonium, [DEA] for diethylammonium, [DEtOHA] for diethanolammonium, [HMIM] for 1-methylimidazolium and [EMIM] for 1-ethyl-3-methylimidazolium:

TABLE 2

Ionic liquids screened.

| Ionic liquid | Type of ionic liquid |
|---|---|
| [TEA][HSO$_4$] | Protic, symmetric, tertiary amine based, weakly coordinating anion |
| [DMBA][HSO$_4$] | Protic, asymmetric, tertiary amine based, weakly coordinating anion |
| [HMIM][HSO$_4$] | Protic, imidazole based, weakly coordinating anion |
| [DEA][HSO$_4$] | Protic, symmetric, secondary amine based, weakly coordinating anion |
| [DEtOHA][Cl] | Protic, symmetric, secondary amine based, alcohol side chain, strongly coordinating anion |
| [HMIM][Cl] | Protic, imidazole based, strongly coordinating anion |
| [EMIM][Cl] | Aprotic, imidazole based, strongly coordinating anion |
| [EMIM][OAc] | Aprotic, imidazole based, strongly coordinating anion |
| [EMIM][OTf] | Aprotic, imidazole based, mildly coordinating anion |

Table 3 displays the copper (II) extraction, saccharification yield as well as pulp and lignin yields after pre-treatment of the copper azole treated softwood with the tested ILs as a percentage of the total initial biomass.

TABLE 3

Results from screening experiments.

| Ionic liquid | Copper extraction/% | Saccharification yield/% | Pulp yield/% | Lignin yield/% |
|---|---|---|---|---|
| [TEA][HSO$_4$] | 87 ± 1 | 55.2 ± 2.6 | 56.7 ± 0.3 | 8.7 ± 0.2 |
| [DMBA][HSO$_4$] | 93 ± 0 | 72.3 ± 4.1 | 42.6 ± 0.3 | 19.4 ± 1.4 |
| [HMIM][HSO$_4$] | 82 ± 1 | 15.7 ± 2.6 | 58.9 ± 0.5 | 7.0 ± 1.7 |
| [HMIM][Cl] | 98 ± 2 | 75.7 ± 2.5 | 43.1 ± 0.8 | 14.3 ± 0.7 |
| [DEA][HSO$_4$] | 85 ± 2 | 0.1 ± 0.1 | 34.7 ± 1.0 | 7.3 ± 0.4 |
| [DEtOHA][Cl] | 81 ± 4 | 11.0 ± 0.3 | 94.5 ± 0.3 | BDL |
| [EMIM][OAc] | 86 ± 2 | 43.0 ± 1.9 | 92.1 ± 1.2 | BDL |
| [EMIM][Cl] | 92 ± 1 | 28.8 ± 2.9 | 75.9 ± 1.8 | 1.7 ± 0.2 |
| [EMIM][OTf] | 68 ± 1 | 9.7 ± 0.3 | 92.7 ± 0.4 | BDL |
| Untreated | — | 9.9 ± 0.2 | 100 | — |

The data shown here suggests that [HSO$_4$]$^-$, [Cl]$^-$ and [OAc]$^-$ ILs are capable of the extraction of 81-98% of the present copper (II) from treated softwood. The only IL studied here that extracted significantly lower amount of copper was [EMIM][OTf] which extracted 68% of the copper (II). A wider range of results was obtained for the saccharification of the recovered cellulose rich pulp; the highest glucose yields were obtained for enzymatic saccharification of [DMBA][HSO$_4$] and [HMIM][Cl] pre-treated biomass (above 70% of theoretical). Lower yields but still significant improvements compared to untreated biomass were obtained with [TEA][HSO$_4$], [EMIM][OAc] and [EMIM][Cl].

CCA Treated Wood

Pre-treatments of chromated copper arsenate (CCA) treated softwood with [HBIM][HSO$_4$], where [HBIM] stands for 1-butylimidazolium, were conducted at 170° C. for 30 min. Saccharification yields obtained were 52.5% and the metal extraction is displayed in table 4. All three metals were extracted nearly quantitatively (≥98%).

TABLE 4

Metal Contents as measured by ICP-OES and relative metal extraction in pulp after [HC$_4$im][HSO$_4$] pre-treatment of the CCA treated wood for 1 hour at 150° C. Standard error of measurements in brackets.

| CCA Treated Wood | Arsenic(V) | Chromium(VI) | Copper(II) |
|---|---|---|---|
| Metal Content/ppm | 4268 (605) | 4664 (745) | 2784 (365) |
| Metal Extracted | 99% (0.06%) | 99% (0.14%) | 98% (0.46%) |

Mixed Infeed and Processed Wood

Mixed unprocessed and processed wood waste obtained (unprocessed wood is chipped waste wood of various origin, processed wood is the same type of wood that had part of the metals, mainly iron, removed mechanically) were pre-treated at 170° C. for 30 min with two different ILs, [HC$_1$im][Cl] and [HC$_1$im][HSO$_4$]. The original metal content as well as the amounts extracted for unprocessed and processed wood are displayed in Tables 5 and 6 respectively.

Higher saccharification yields were obtained with [HC$_1$im][Cl] and measured to be 53 and 60% for unprocessed and processed wood respectively.

TABLE 5

Metal Contents as measured by ICP-OES and relative metal extraction in pulp after pre-treatment of the unprocessed mixed wood. Standard error of measurements in brackets.

| Unprocessed Mixed Wood | Zinc(II) | Lead(II) | Iron(II/III) | Chromium(VI) | Copper(II) |
|---|---|---|---|---|---|
| Metal Content/ppm | 138 (0.3) | 173 (8.4) | 567 (12.4) | 9.1 (1.2) | 37 (6.9) |
| Metal Extracted with [HC$_1$im][HSO$_4$] | 82% (1.50%) | 12% (1.85%) | 55% (3.67%) | 69% (1.71%) | 54% (2.07%) |
| Metal Extracted with [HC$_1$im][Cl] | 86% (3.02%) | 85% (1.29%) | 65% (4.67%) | 80% (3.46%) | 90% (0.59%) |

TABLE 6

Metal Contents as measured by ICP-OES and relative metal extraction in pulp after pre-treatment of the processed mixed wood. Standard error of measurements in brackets.

| Processed Mixed Wood | Zinc(II) | Lead(II) | Iron(II/III) | Chromium(VI) | Copper(II) |
|---|---|---|---|---|---|
| Metal Content/ppm | 114 (0.3) | 367 (18.7) | 331 (31.7) | 55 (2.1) | 82 (5.0) |
| Metal Extracted with [HC$_1$im][HSO$_4$] | 70% (6.20%) | 39% (4.47%) | 52% (14.86%) | 77% (2.66%) | 48% (2.74%) |
| Metal Extracted with [HC$_1$im][Cl] | 89% (0.41%) | 96% (1.92%) | 56% (9.28%) | 93% (0.54%) | 97% (0.29%) |

The presented results suggest very high extraction efficiencies in the range of 80-99%, for zinc (II), lead (II), chromium (VI) and copper (II) are possible with [HC$_1$im][Cl] in the absence of a chelating agent.

EXAMPLE 2 COPPER SOLUBILITY AND ELECTRODEPOSITION OF COPPER FROM VARIOUS IONIC LIQUIDS COPPER SOLUBILITY

Solubility measurements were conducted in order to establish solubility limits in one of the investigated protic ionic liquids 1-methylimidazolium hydrogen sulfate ([HC$_1$im][HSO$_4$], shown below, top). For comparison, solubility was also tested in the more inexpensive triethylammonium hydrogen sulfate [TEA][HSO$_4$] (shown below, bottom).

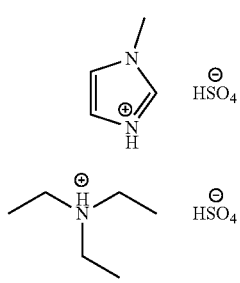

[HC$_1$im][HSO$_4$], top and [TEA][HSO$_4$], bottom.

The solubilities were tested by dissolving copper oxide in the ionic liquid until no further dissolution was observed overnight. The remaining solids were filtered off and the obtained solutions subjected to ICP-OES. In order to investigate if excess base improved solubilities, 5 wt % excess amine/imidazole was used in a further test. The results are displayed in FIG. 3. The maximum copper(II) solubilities at 20 wt % water are also summarised in table 7.

TABLE 7

Copper(II) solubilities in ionic liquid systems at 20 wt % water.

| Ionic Liquid | Copper(II) solubility/ppm |
|---|---|
| [HC$_1$im][HSO$_4$] | 4752 ± 715 |
| [TEA][HSO$_4$] | 2043 ± 433 |
| [HC$_1$im][HSO$_4$] 5% excess base | 10845 ± 2050 |
| [TEA][HSO$_4$] 5% excess base | 13712 ± 4068 |

Figure 3:
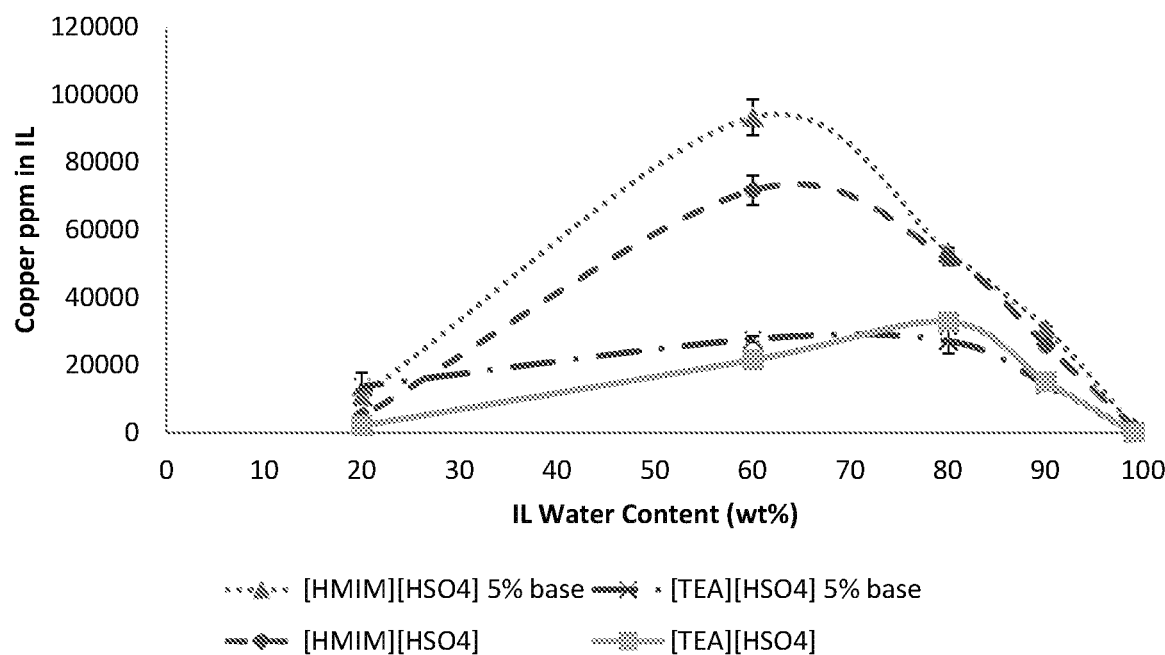
FIG. 3 shows copper (II) concentrations in IL measured by inductively coupled plasma optical emission spectrophotometry ICP OES

FIG. 3 shows that the water content plays a deciding role in the copper dissolution capability of the ionic liquid. Solubility peaks at around 60 wt % and 80 wt % water in the case of [HC$_1$im][HSO$_4$] and [TEA][HSO$_4$] respectively. Peak solubility is around 72,000 ppm or 7.2 wt % in the case of [HC$_1$im][HSO$_4$] and 33,000 ppm or 3.3 wt % in the case of [TEA][HSO$_4$]. At higher base contents the dissolution capacity of [HC$_1$im][HSO$_4$] is improved to around 93,000 ppm or 9.3 wt % at 60 wt % water. Pre-treatments however cannot be conducted at water contents above around 30% which means that solubilities at around 20 wt % water are more important for the here conducted study. From table 7 we can see that at 20 wt % water the solubility in [HC$_1$im][HSO$_4$] was improved from 4752 ppm to 10845 ppm by the addition of 5% excess base while in the case of [TEA][HSO$_4$] dissolution capability was improved from 2043 ppm to 13712 ppm. [HC$_1$im][HSO$_4$] and [TEA][HSO$_4$] with 5 wt % excess base therefore reach a similar dissolution capacity within the measurement error.

While these tests were conducted by dissolving Cu(II) oxide, copper bound in the biomass is expected to be extracted in a similar manner.

Electrochemical properties of [HC$_1$im][HSO$_4$]

Figure 4:
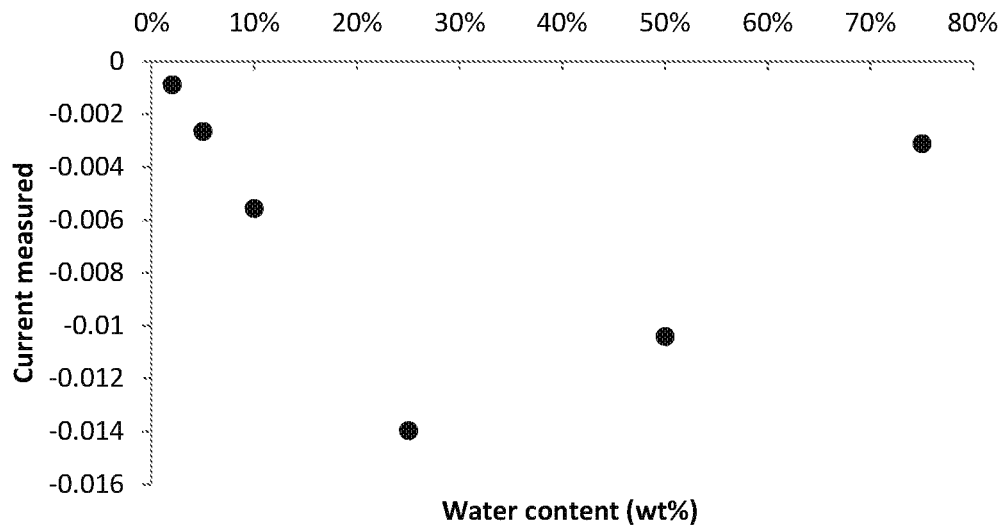
FIG. 4 shows currents measured at −1V in [HC$_1$im][HSO$_4$].

For a successful deposition of copper from the ionic liquid, electrochemical stability of the IL needs to be guaranteed in order to make the process viable. FIG. 4 shows maximum currents obtained at −1 V vs. Ag in [HC$_1$im][HSO$_4$] with different water contents. The almost dry IL (2 wt % water) shows very small currents at very reducing potentials, suggesting that the ionic liquid is electrochemically stable under these conditions. The higher water content ILs exhibit higher current densities due to the occurrence of water reduction leading to hydrogen evolution. The current density reaches a maximum at 25 wt % water and then decreases again. The hydrogen evolution reaction can be linked to acidity of the medium. The data presented here suggest that acidity of the ionic liquid maximises at around 25 wt % water.

Copper Deposition

The deposition of copper out of an ionic liquid liquor was shown for [HC$_1$im][HSO$_4$] as well as for the less expensive triethylammonium hydrogen sulfate ([TEA][HSO$_4$]) by means of cyclic voltammetry and chronoamperometry. In both cases, liquor from biomass pre-treatment was saturated with copper (II) ions by dissolution of CuO and filtering off undissolved solid. The liquors tested contained 20 wt % water in order to mimic the conditions of pre-treatment.

Figure 5:
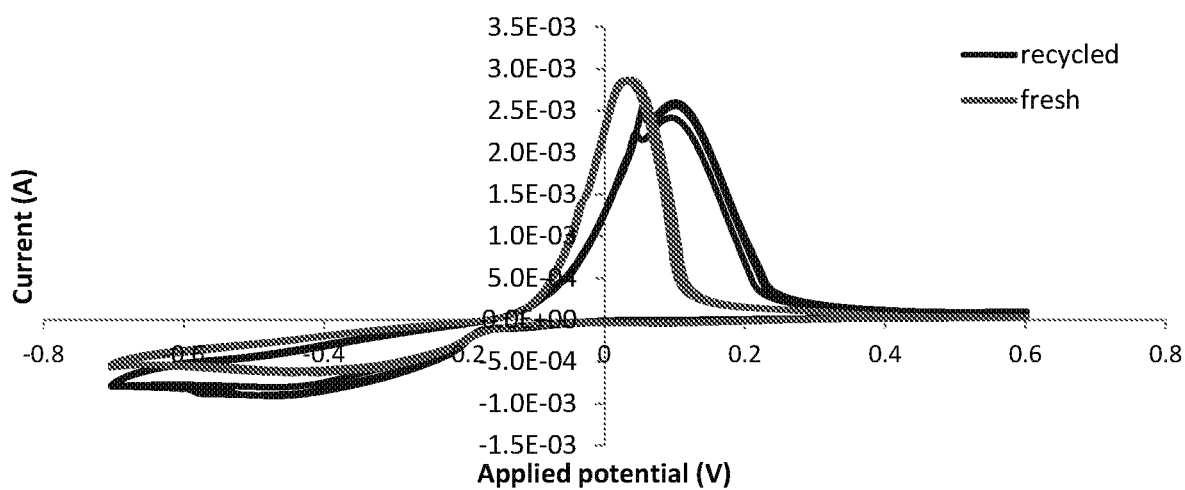
FIG. 5 shows cyclic voltammograms of recycled and fresh [HC$_1$im][HSO$_4$] doped with CuO to saturation.

Preliminary results of solubility tests of CuO in the two protic ionic liquids show a higher solubility in the imidazolium salt than in the alkylammonium salt. Therefore the focus of further tests has been on the imidazolium salt. In order to establish the effect of biomass degradation products present in the liquor on the deposition behaviour of copper, a cyclic voltammogram (FIG. 5) of copper (II) saturated fresh ionic liquid was compared to that obtained from the copper (II) saturated recycled ionic liquid. The oxidation current peak due to Cu→Cu$^{II}$+2e$^-$ at ca. 0.1 V in the positive-going voltammetric scan of the recycled liquor was shifted slightly towards higher potentials compared to the fresh ionic liquid and exhibited a small side peak before the main peak. However, the potentials (ca. −0.15 V) of current onsets for the oxidation (Cu→Cu$^{II}$+2e$^-$) and reduction (Cu$^{II}$+2e$^-$→Cu) were almost identical. Integration of current-time data further confirmed that the copper deposition was not measurably affected by biomass degradation products, as charge efficiencies in both cases were around 94% under the tested conditions.

The invention claimed is:

1. A process for the extraction of metal pollutants from treated lignocellulosic biomass, the process comprising
   (a) contacting the treated lignocellulosic biomass with an ionic liquid, said ionic liquid comprising an anion and an organic cation, wherein the contacting produces a cellulose-rich solid material and a liquid phase, wherein the liquid phase comprises a hemicellulose fraction, a lignin fraction, and metal pollutants, the anion is selected from the group consisting of chloride (Cl$^-$), acetate ([OAc]$^-$), and hydrogen sulfate (HSO4]$^-$) and the cation is selected from (i) a cation of general formula:

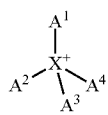

wherein X is N; and
A1 to A4 are each independently selected from H, an aliphatic, C3-6 carbocycle, C6-10 aryl, alkylaryl, and heteroaryl; or
(ii) a cation containing a nitrogen-containing heterocyclic moiety.

2. The process of claim 1 wherein the cation is selected from (i) a cation of general formula:

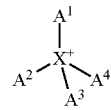

wherein X is N; and
A1 to A4 are each independently selected from H, an aliphatic, C3-6 carbocycle, C0-10 aryl, alkylaryl, and heteroaryl.

3. The process of claim 2 wherein at least one of A1 to A4 is H.

4. The process of claim 1 wherein the organic cation is a protic organic cation.

5. The process of claim 1 wherein the cation is an alkylammonium, an alcoholammonium, or a mixture thereof.

6. The process of claim 5 wherein the cation is N,N-dimethyl-N-butylammonium ([DMBA]$^+$).

7. The process of claim 1 wherein the cation containing a nitrogen-containing heterocyclic moiety is an imidazolium based cation or a mixture thereof.

8. The process of claim 7 wherein the imidazolium based cation is selected from 1-ethyl-3-methylimidazolium ([EMIM]$^+$), 1-butylimidazolium ([HBIM]$^+$) and 1-methylimidazolium ([HMIM]$^+$).

9. The process of claim 1 wherein the ionic liquid is selected from N,N-dimethyl-N-butylammonium hydrogen sulfate ([DMBA][HSO4]), 1-butylimidazolium hydrogen sulfate ([HBIM][HSO4]), 1-methylimidazolium chloride ([HMIM]C I), 1-methylimidazolium hydrogen sulfate ([HMIM][HSO4]), or triethylammonium hydrogen sulfate ([TEA][HSO4]), or mixtures thereof.

10. The process of claim 1 wherein the organic cation is derived from its conjugate base, and wherein the ionic liquid comprises at least 5% molar excess of the conjugate base.

11. The process of claim 1 wherein the ionic liquid is contacted with the biomass in the form of a composition comprising the ionic liquid and 10-40% v/v water.

12. The process of claim 1 further comprising
   (b) separating the cellulose-rich solid material from the liquid phase.

13. The process of claim 12 further comprising
   (c(i)) washing the cellulose-rich solid material at least once with a washing fluid that is the ionic liquid or an organic solvent miscible with the ionic liquid.

14. The process of claim 13 further comprising
   (c(ii)) separating the cellulose-rich solid material from the washing fluid.

15. The process of claim 12 further comprising
   (d) adding an anti-solvent to the ionic liquid obtained in (b) to precipitate the lignin.

16. The process of claim 12 further comprising removing water from the ionic liquid after step (b).

17. The process of claim 15 further comprising removing water from the ionic liquid after step (d).

18. The process of claim 1 further comprising electrodeposition of the metal pollutant from the ionic liquid.

19. The process of claim 18 wherein after the electrodeposition, the ionic liquid is re-used in step (a).

20. The process of claim 13 further comprising electrodeposition of the metal pollutant from the ionic liquid, wherein after the electrodeposition, the ionic liquid is re-used in step (c(i)).

21. The process of claim 1 further comprising saccharification of the cellulose containing solid residue obtained in step (a) to obtain glucose.

22. The process of claim 12 further comprising saccharification of the cellulose containing solid residue obtained in step (b) to obtain glucose.

23. The process of claim 14 further comprising saccharification of the cellulose containing solid residue obtained in step (c(11)) to obtain glucose.

24. A method of fractionating lignocellulosic biomass, the method comprising:
(a) contacting the lignocellulosic biomass with an ionic liquid, said ionic liquid comprising an anion and a N,N-dimethyl-N-butylammonium ([DMBA]$^+$) cation.

25. The method of claim 24, wherein the ionic liquid is N,N-dimethyl-N-butylammonium hydrogen sulfate ([DMBA][HSO4]).

* * * * *